US011638631B2

(12) United States Patent
Berner

(10) Patent No.: US 11,638,631 B2
(45) Date of Patent: May 2, 2023

(54) PROCESS FOR PROVIDING A DENTAL ARTICLE

(71) Applicant: STRAUMANN HOLDING AG, Basel (CH)

(72) Inventor: Simon Berner, Basel (CH)

(73) Assignee: STRAUMANN HOLDING AG, Basel (CH)

(*) Notice: Subject to any disclaimer, the term of this patent is extended or adjusted under 35 U.S.C. 154(b) by 397 days.

(21) Appl. No.: 16/612,176

(22) PCT Filed: Apr. 24, 2018

(86) PCT No.: PCT/EP2018/060466
§ 371 (c)(1),
(2) Date: Nov. 8, 2019

(87) PCT Pub. No.: WO2018/206286
PCT Pub. Date: Nov. 15, 2018

(65) Prior Publication Data
US 2020/0367996 A1 Nov. 26, 2020

(30) Foreign Application Priority Data
May 9, 2017 (EP) .................................... 17170216

(51) Int. Cl.
A61C 8/00 (2006.01)
A61L 2/14 (2006.01)
(Continued)

(52) U.S. Cl.
CPC .......... A61C 8/0015 (2013.01); A61C 8/0012 (2013.01); A61C 8/0087 (2013.01);
(Continued)

(58) Field of Classification Search
CPC ... A61C 8/0015; A61C 8/0012; A61C 8/0087; A61L 2/14; A61L 2/208
See application file for complete search history.

(56) References Cited

U.S. PATENT DOCUMENTS 5,087,418 A * 2/1992 Jacob ..................... A61L 2/14
422/906
6,165,925 A 12/2000 Rieger
(Continued)

FOREIGN PATENT DOCUMENTS

EP 0 388 576 A1 9/1990
EP 1 847 278 A1 10/2007
(Continued)

OTHER PUBLICATIONS

Jun. 26, 2018 International Search Report issued in International Patent Application No. PCT/EP2018/060466.
(Continued)

Primary Examiner — Ralph A Lewis
(74) Attorney, Agent, or Firm — Oliff PLC

(57) ABSTRACT

A process for providing a sterilized dental article, at least a portion of the surface of which exhibiting a contact angle of less than 45°. The process includes the subsequent steps of a) providing a dental article and b) subjecting the initial dental article to a hydrogen peroxide plasma treatment. It is characterized in that the hydrogen peroxide plasma sterilization treatment of step b) is carried out in the presence of a carbon-containing compound, which during treatment is converted to form a carboxylic group attached to the surface of the dental article.

20 Claims, 1 Drawing Sheet

(51) Int. Cl.
  *A61L 2/20*      (2006.01)
  *A61L 101/02*    (2006.01)
(52) U.S. Cl.
  CPC .............. *A61L 2/14* (2013.01); *A61L 2/208*
        (2013.01); *A61C 2008/0046* (2013.01); *A61C*
        *2202/00* (2013.01); *A61L 2101/02* (2020.08);
           *A61L 2202/182* (2013.01); *A61L 2202/21*
                                              (2013.01)

(56) References Cited

U.S. PATENT DOCUMENTS

2005/0260107 A1* 11/2005 Jackson .............. C11D 11/0005
                                                      422/136
2005/0268573 A1* 12/2005 Yan ........................ A61B 50/30
                                                       53/425
2010/0297582 A1* 11/2010 Hofstetter ............ A61C 8/0012
                                                      433/173

FOREIGN PATENT DOCUMENTS

EP       1 982 670 A1    10/2008
KR      2006 0110190 A   10/2006
KR        10-1584506 B1   1/2016

OTHER PUBLICATIONS

Jun. 26, 2018 Written Opinion of the International Searching Authority issued in International Patent Application No. PCT/EP2018/060466.

* cited by examiner

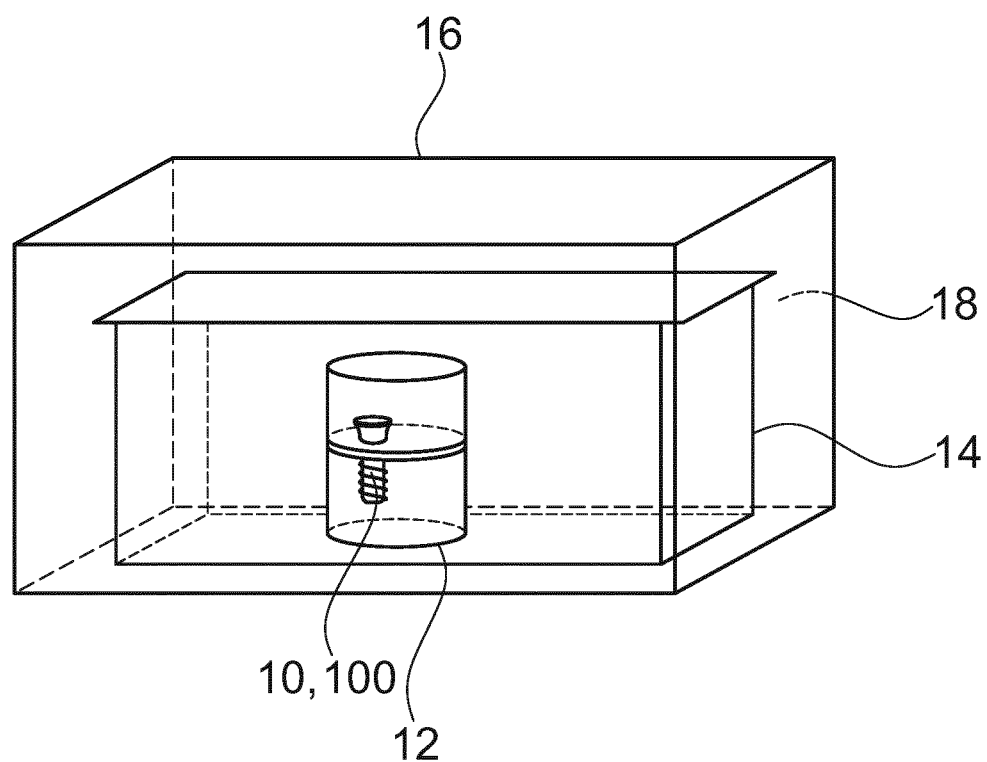

PROCESS FOR PROVIDING A DENTAL ARTICLE

The present invention relates to a process for providing a dental article. The invention further relates to a dental article obtainable by the process and to a dental article system comprising the dental article. Still further, the invention relates to the use of a hydrogen peroxide plasma treatment for improving the hydrophilicity of a dental article and/or for improving the storage stability of the hydrophilicity of a dental article.

It is commonly known that dental articles must meet strict requirements regarding biocompatibility and mechanical stability of the material involved. Specifically with regard to dental implants, which are inserted into the human jawbone, also a fast and strong osseointegration, i.e. a direct structural and functional connection between living bone and the implant's surface, has been found to be a decisive factor for a successful outcome of the implantation procedure.

It is also common knowledge that dental articles must be sterile when being brought into contact with a patient's body. To this end, the dental article is typically sterilized and stored in the sterile interior space of a packaging, which remains closed until use of the article by the dentist.

In theory, different sterilization techniques can be applied. According to the most common approach, the dental article is subjected to heat sterilization using steam. This technique is typically performed in a steam sterilizer (also referred to as autoclave) using steam typically having a temperature above 120° C. under pressure.

Heat sterilization is, however, not suitable if the dental article to be sterilized is heat-sensitive or if further heat-sensitive components are present during sterilization. For example, heat sterilization is not suitable for a dental implant which is already packaged, since the packaging material is typically sensitive towards the sterilization temperature applied. In addition, the use of steam is unsuitable if during sterilization components are present that are soluble in water.

As an alternative to the mentioned heat sterilization, the dental article can be subjected to ethylene oxide gas sterilization or plasma sterilization. These techniques can be applied on a dental article that is packaged already. However, sterilization of an already packaged article requires the packaging to be gas-permeable, in order to allow permeation of the ethylene oxide gas or the plasma used for sterilization. In as far as ethylene oxide is used, the technique has the further drawback of requiring relatively strict safety measures due to the high toxicity of the sterilizing agent.

Further sterilization techniques include radiation sterilization, in particular gamma-sterilization or X-ray sterilization.

Apart from being sterile, dental articles are typically also required to exhibit a high hydrophilicity, indicated by a relatively low contact angle of the surface when being in contact with water. For dental implants, for example, a high hydrophilicity has been shown to go along with a good osseointegration and ultimately a relatively short healing time after insertion of the implant.

Different approaches for improving the hydrophilicity of a dental article have been suggested. These approaches may vary depending on the material the dental article is made of.

For titanium implants, for example, it has been found that surfaces prepared according to the SLA® technology exhibit a very high hydrophilicity immediately after preparation. The respective technology is for example described in EP-A-0 388 576.

EP-A-1 982 670 refers to a process for providing a surface topography on a ceramic dental implant and it has been found that the ceramic surface obtained also exhibits a high hydrophilicity.

Despite the high hydrophilicity that is present immediately after the process described in EP-A-0 388 576 or EP-A-1 982 670, respectively, its preservation can be a challenging task. This is due to hydrophilicity decreasing relatively rapidly when the dental article is exposed to air, owed to the deposition of organic compounds present in the air on the surface of the article.

For the sterilization techniques mentioned above, the sterilizing gas or plasma is required to permeate the packaging, in order to reach the dental article to be sterilized. Given this mandatory gas permeability of the packaging, also organic compounds of relatively low molecular weight may pass the packaging material and bind to the dental article's surface, thereby lowering its hydrophilicity. This decrease in hydrophilicity is in particular an issue when storing the dental article over relative long periods during which organic compounds can accumulate on the surface.

In the context of titanium implants, the problem of maintaining the hydrophilicity of the implant is addressed in EP-A-1 847 278. EP-A-1 847 278 describes a process, which makes use of the SLA® technology, and—in order to preserve the hydrophilicity achieved thereby—suggests a protective layer to be formed on the implant body. This protective layer shall prevent the deposition of contaminants on the surface of the implant and is configured such that it dissolves on contact with bodily fluid or on contact with the bone.

EP-A-1 847 278 mentions the possibility of cleaning the implant by a UV/ozone treatment or by a plasma treatment. In both cases, the SLA® surface is neutralized in water and dried in air at 80° C. to 110° C. before the mentioned cleaning steps. The cleaned implants are then immediately immersed in a NaCl solution, before being removed from the solution and dried with nitrogen.

On the one hand, the process described in EP-A-1 847 278 has the disadvantage that it is relatively laborious, requiring the formation of a protective layer. In addition, the process requires measures to be taken to safeguard that the surface is and remains sterile during formation of the protective layer and that the protective layer itself is sterile as well.

On the other hand, current gas or plasma sterilization techniques without a protective layer do not allow a hydrophilic surface to be maintained over a long period, since organic contaminants accumulate on the surface over time, as mentioned above.

In consideration of the above, the object of the present invention is to provide a simple process for the treatment of a dental article, which results in a high hydrophilicity of the dental article also after storing over a relatively long period. Specifically, at least a portion of the dental article's surface shall exhibit a contact angle of less than 45° even after a storage period of more than 12 months.

In addition, the process shall further allow to sterilize the dental article in one and the same process step of providing the long-term hydrophilicity mentioned above.

The object is achieved by the process disclosed and claimed herein. Preferred embodiments of the process of the present disclosure are also described below.

The process includes the subsequent steps of a) providing an initial dental article and b) subjecting the initial dental article to a hydrogen peroxide plasma treatment.

According to the invention, the hydrogen peroxide plasma treatment of step b) is carried out in the presence of a carbon-containing compound, which during treatment is converted to form a carboxylic group attached to the surface of the dental article.

In the context of the present invention, it has surprisingly been found that by treating the surface with a hydrogen peroxide plasma in the presence of a carbon-containing compound, the hydrophilicity of the surface is increased.

Quite in contrast to the established doctrine, the increase of the hydrophilicity achievable by the present invention does not correlate with a decrease in the amount of carbon present on the surface. Rather, the surface modification, namely the functionalization of the surface with carboxylic groups obtained in step b), gives rise to an increase in hydrophilicity.

Apart from that, it has further been found that the high hydrophilicity achieved by the present invention is also stable over a relatively long period.

Typically, an adventitious carbon-containing contamination layer is present on the initial dental article. This allows the process of the present invention to be performed in a very simple and straightforward manner, since the carbon-containing compounds contained in the contamination layer can form the basis for the carboxylic groups to be formed and attached to the surface of the dental article in step b). There is, therefore, no need to actively add a carbon-containing compound in step b), since it is normally already present in the form of the adventitious contamination layer.

In contrast to the approaches taught by the state of the art to remove the adventitious carbon-containing contamination layer (which is generally considered harmful for obtaining a high hydrophilicity), the concept of the present invention, thus, goes into a completely opposite direction by making use of the contamination layer as a basis for a functionalization of the surface to furnish it with a long-term hydrophilicity.

By the feature that the carbon-containing compound is present on the surface of the initial dental article, and in particular adheres to the surface, the present invention is also distinct from the process disclosed in US 2005/260107 A1, relating to the cleaning of a substrate using percarbonic acid, which is generated by contacting hydrogen peroxide and gaseous carbon dioxide in the presence of a plasma or UV radiation.

Ultimately, a dental article can thus be provided which allows for establishing a fast and strong interaction with the surrounding tissue, specifically bone as well as soft tissue, depending on the nature and intended purpose of the specific article.

As mentioned, the hydrophilicity of the surface of the dental article is increased in step b). Specifically, the surface of the dental article obtained in step b) has a contact angle of less than 45° and is therefore hydrophilic or superhydrophilic.

Within the context of the present invention, the term "hydrophilic" is used for a surface exhibiting a contact angle of less than 45°, whereas for a contact angle of less than 10° the term "superhydrophilic" is used.

Superhydrophilicity, i.e. a contact angle of less than 10°, is typically present immediately after step b) and can after a storage period of several months rise to a level of higher than 10°. After several months storage, the surfaces nevertheless still exhibit a contact angle of less than 45° and therefore still fall within the definition of a hydrophilic surface.

Typically, the hydrophilicity obtained in step b) is higher than the one of the dental article provided in step a). In other words, the contact angle obtained in step b) is preferably lower than the contact angle present in step a).

The term "contact angle" as used in the context of the present invention relates to the contact angle of water on the surface, i.e. to the angle formed at the interface where water meets the surface. Thereby, "water" used for the contact angle measurement relates to pure water, specifically ultra-pure water. In particular, the contact angle measurement is carried out by the sessile drop method (e.g. by means of a device of the type EasyDrop DSA20E, Krüss GmbH) using a drop size of 0.3 µl. Contact angles were calculated by fitting a circular segment function to the contour of the droplet placed on the surface.

By the feature that the surface of the dental article provided by the process of the present invention exhibits a contact angle of less than 45°, preferably less than 20°, more preferably less than 10°, it is meant that this contact angle is present at least immediately after the hydrogen peroxide plasma treatment.

Hydrogen peroxide plasma treatments as well as devices for carrying out these treatments have been used in the past for sterilizing purposes and are known to the skilled person. Specifically, the hydrogen peroxide plasma treatment according to step b) of the present invention can be carried out using a Sterrad® device, such as Sterrad® 200 GMP using 59% $H_2O_2$ or Sterrad® 100 NX using 95% $H_2O_2$.

As will be discussed in more detail by way of the specific examples below, both the increase in hydrophilicity as well as its stability over time are achievable by using hydrogen peroxide plasma only, but not by other plasma treatments, which could potentially be used for cleaning or sterilization, such as $O_2$ plasma treatment and $ArH_2$ plasma treatment.

In contrast to the methods taught in the state of the art, namely in EP-A-1 847 278 mentioning the possibility of cleaning the implant by a UV/ozone treatment or by a plasma treatment, the present invention does not require the surface of the dental article to be devoid of organic contaminants, but rather requires at least a minor number of carbon-containing compounds to be present. The process of the present invention is therefore very simple and straightforward in that no laborious measures for protecting the surface from any such contaminants need to be taken. Rather, it has been proven sufficient to subject the surface of the dental article to be provided in step a) to a simple cleaning step with a minor number of carbon-containing compounds remaining on the surface.

According to a particularly preferred embodiment, the hydrogen peroxide plasma treatment of step b) is carried out in a manner to sterilize the dental article, thus allowing to obtain a dental article, which is both long-term hydrophilic and sterile, in one and the same process step. Preferably, the process of the present invention is, thus, devoid of any separate functionalization step after sterilizing the dental article in step b).

Apart from this preferred embodiment, the present invention also encompasses embodiments in which an additional sterilization treatment is performed before or after the hydrogen peroxide plasma treatment. In particular, embodiments are encompassed in which the initial dental article is subjected to an ethylene oxide sterilization treatment before the hydrogen peroxide plasma treatment. In this particular embodiment, sterilization of the dental article is maintained, but any adverse effect on the hydrophilicity caused by the sterilization is reversed.

The surprising finding of hydrogen peroxide plasma sterilization allowing for both a sterile and hydrophilic dental article opens the possibility of a simple process for further extending the storage stability of these properties, beyond the already high storage stability mentioned above.

According to a further aspect, the present invention thus also relates to a process for providing a dental article, at least a portion of the surface of which exhibiting a contact angle of less than 45°, the process comprising the subsequent steps of
a) providing an initial dental article and
b) subjecting the initial dental article to a hydrogen peroxide plasma treatment,
characterized in that in a further step
c) the dental article obtained in step b) is packed in a packaging enclosing an interior space, said interior space being sealed from the outside space surrounding the packaging in a gas-tight manner.

The packaging according to step c) therefore prevents both hydrocarbon compounds, which may impair the dental article's hydrophilicity, as well as biological contaminants, which would destroy the sterilization effect, from entering the interior space and getting in contact with the dental article's surface. Ultimately, a very high storage stability can be achieved, allowing to maintain the dental article's hydrophilicity for a term longer than 12 months, preferably longer than 2 years, more preferably longer than 4 years.

To safeguard that a high hydrophilicity is maintained, it is preferred that the packing according to step c) is performed immediately after the treatment according to step b). Within the context of the present invention, the term "immediately after the treatment" is to be understood as less than 2 weeks, preferably less than 1 week after the treatment.

In order to safely hold the dental article in place, and in particular to safely prevent the dental article from coming into contact with any material of a container or packaging, it is preferably placed in a holding container before subjecting it to the treatment according to step b).

According to a preferred embodiment, step a) therefore includes the sub-step of
a') placing the initial dental article in a holding container which is open in a manner such to allow hydrogen peroxide gas and plasma to get in contact with at least a part of the surface of the dental article.

Typically, the holding container is made of a material selected from the group consisting of cyclic olefin copolymer (COC), polyethylene (PE), polypropylene (PP), polyether ether ketone (PEEK) and Teflon®; no negative impact of these materials being present during hydrogen peroxide plasma sterilization treatment has been detected in the course of the present invention.

In general, the initial dental article is arranged in a sterilization container before being subjected to the hydrogen peroxide plasma treatment of step b) and, optionally, also before any sterilization treatment performed in addition to the hydrogen peroxide plasma treatment. The membrane material of the sterilization container is gas-permeable in order to allow permeation of the sterilizing gas and plasma. It is however, impermeable to any biologic agent, such as bacteria, viruses, prions, fungi as well as their spore forms. Thus, the sterilization container forms a sterile barrier and after sterilization keeps the dental article in a sterile environment.

According to a particularly preferred embodiment, step b) of the process thus includes prior to the hydrogen peroxide plasma treatment the further sub-step of
b') arranging the initial dental article, optionally placed in a holding container, in a sterilization container, which is closed and which comprises a membrane material that is permeable to hydrogen peroxide gas and plasma.

After the hydrogen peroxide plasma treatment, the dental article is preferably stored in the sterilization container, and it has been found that storing in the sterilization container without an additional gas-impermeable packaging is sufficient for maintaining a high hydrophilicity for a period of about 1 year or even more. If an even higher storage stability is desired, the sterilization container with the dental article arranged therein is placed in the gas-impermeable packaging, as mentioned above.

According to a very simple and straightforward embodiment, which is explicitly encompassed by the present invention, the sterilizing container is only partially made of a gas-permeable membrane material, whereas the other part is made of a gas-impermeable material. In order to obtain the interior space according to step c), which is sealed from the outside space surrounding the packaging in a gas-tight manner, it is therefore sufficient to merely cover the gas-permeable membrane material with a gas-impermeable sealing, such as a sealing foil or sheet.

Thus, the present invention specifically also relates to a process comprising the subsequent steps of
α) providing an initial dental article by placing it in a holding container, which is designed to hold the dental article in place and is open in a manner such as to allow hydrogen peroxide gas and plasma to get in contact with at least a part of the surface of the dental article,
β) arranging the initial dental article placed in the holding container according to step a) in a sterilization container, which is closed and which comprises a membrane material that is permeable to hydrogen peroxide gas and plasma, and subjecting the initial dental article to a hydrogen peroxide plasma treatment, and
γ) covering the permeable membrane material of the sterilization container by a gas-impermeable sealing, thereby obtaining a packaging enclosing an interior space, said interior space being sealed from the outside space surrounding the packaging in a gas-tight manner.

As mentioned above, the process of the present invention allows sterilizing a dental implant and improving its hydrophilicity in one single process step and maintaining these characteristics during long term storage. As also mentioned, an increase in the hydrophilicity is in particular achieved, if carbon-containing compounds are present on the surface of the dental article. In other words, the effect of the process of the present invention is also achievable, if the dental article to be treated has been exposed to air and due to this exposure has suffered a decrease in the surface's hydrophilicity due to an adventitious contamination layer formed on the surface. There is therefore no need to clean the surface from hydrocarbon contaminants prior to the process.

Apart from the above-mentioned embodiment, according to which the carbon-containing compound is present in the form of an adventitious contamination layer formed on the surface, the present invention also encompasses embodiments, in which the carbon-containing compound is actively deposited on the surface of the initial dental article. For these embodiments, the process thus comprises prior to step b) a further sub-step of depositing a carbon-containing compound onto the surface of the initial dental article.

As further mentioned above, step β) can include an additional sterilization treatment before or after the hydrogen peroxide plasma treatment.

According to a specific embodiment, the dental article to be treated according the present invention, thus, contains carbon-containing compounds on its outermost surface, which is in complete contradiction to the established doctrine, according to which the surface must be devoid of any carbon contamination in order to exhibit a high hydrophilicity. The amount of carbon on the outermost surface can e.g. be determined by XPS (X-ray Photoelectron Spectroscopy) and is typically in a range from 3 to 55 at. %, preferably in the range from 10 to 40 at. %.

Preferably, the dental article is made of metal or ceramic. In particular, it is a metallic or ceramic component of a dental implant system, more particularly a dental implant or a dental implant abutment.

The advantages achievable by the present invention are particularly pronounced, if the dental article is made of ceramic. This is not only due to the hydrophilicity increase achieved by the hydrogen oxide plasma sterilization being particularly high on ceramic. Given that the interior enclosed by the packaging according to step c) is sealed from the outside space in a gas-tight manner, no water molecules permeate the packing and the humidity in the interior space can therefore be kept at a very low level. Thus, the problem of a ceramic dental article suffering hydrothermal aging are according to this embodiment efficiently circumvented.

According to a particularly preferred embodiment, the dental article is made of zirconia, and more particularly is made of yttria-stabilized zirconia. By using yttria-stabilized zirconia, a dental article having a particularly high mechanical strength can be achieved.

In this regard, the term "yttria-stabilized zirconia" encompasses—besides purely yttria-stabilized zirconia—any yttria-stabilized zirconia that is co-stabilized with a co-stabilizing agent, such as cerium, calcium, erbium and/or magnesium or their respective oxides.

Also, the term "yttria-stabilized zirconia" encompasses both a material based on zirconia particles co-precipitated with yttria as well as a material based on yttria-coated zirconia particles.

An example of an yttria-stabilized zirconia based on zirconia particles co-precipitated with yttria is $ZrO_2$-TZP/TZP-A Bio-HIP® ($ZrO_2$) Bioceramic of Metoxit AG, Switzerland. The composition of this ceramic material comprises 92.1 to 93.5 weight-% $ZrO_2$, 4.5 to 5.5 weight-% $Y_2O_3$, 1.8 to 2.2 weight-% $HfO_2$ and 0.25 weight-% $Al_2O_3$. It offers a particularly high mechanical stability and strength, in particular when prepared by hot isostatic pressing or by sintering with subsequent hot isostatic densification. A detailed description of the ceramic material is given in U.S. Pat. No. 6,165,925, the disclosure of which is incorporated herein in its entirety by reference.

Apart from yttria-stabilized zirconia, also e.g. ceria-stabilized or magnesia-stabilized zirconia as well as zirconia stabilized with strontium, ytterbium, gadolinium, calcium, erbium or neodymium or their oxides, respectively, are thinkable and also encompassed by the term "ceramic" according to the present invention.

As mentioned, the dental article can also be made of metal. It is in this regard particularly preferred that the dental article is made of titanium, niobium, hafnium, tantalum, vanadium, aluminum, steel or alloys thereof. Most preferably, the metal dental article is made of titanium or a titanium alloy; these materials have the necessary strength for withstanding the mechanical loads that occur, and they are at the same time sufficiently biocompatible for osseointegration and long-term use in the mouth.

With regard to the use of a titanium alloy as material of the dental article, a titanium zirconium alloy comprising from about 13 to about 17 wt.-% of zirconium is particularly preferred. An example of a highly suitable titanium zirconium alloy is Roxolid®, which consists of about 85 wt.-% of titanium and about 15 wt.-% of zirconium.

As also mentioned above, the dental article is preferably a dental implant or a dental implant abutment, since for these dental articles, a high hydrophilicity is of particular importance for establishing a fast and strong interaction with the surrounding bone. In particular, a good osseointegration can be achieved for a dental implant treated according to the process of the present invention, whereas a good soft tissue interaction can be achieved if the dental article is a dental implant abutment.

Alternatively or additionally, the dental article can also be a metallic or ceramic tool for installing the dental implant system. In particular, the dental article can be a kit of parts comprising a dental implant and insertion tool for inserting the dental implant.

According to a further preferred embodiment, the surface of the dental article, and in particular of the dental implant, is roughened. To this end, the dental article is before step a) subjected to a surface pre-treatment comprising
sandblasting the surface, followed by
acid etching the sandblasted surface.

In combination with the high and stable hydrophilicity obtainable by the present invention, the surface topography achieved by this surface pre-treatment has been found to be highly osseointegrative, i.e. to provide a fast and strong interaction with the bone. For the particularly preferred embodiment mentioned above, in which the dental article is made of ceramic, an etching solution containing hydrofluoric acid is preferably used.

As mentioned above, the surface of a dental article treated according to the present invention is functionalized by carboxylic groups generated during hydrogen peroxide plasma sterilization treatment.

According to a further aspect, the present invention therefore also relates to a sterilized dental article obtainable by the process described above, the surface of said dental article being at least partially functionalized with carboxylic groups attached thereto. As mentioned above, it has been found that a carboxyl-functionalized surface exhibits a contact angle of less than 20° directly after treatment and that a contact angle of less than 45° is still present after 12 months of storage. The dental article can theoretically be any article used in oral implantology, but is preferably an article for which not only sterility, but also hydrophilicity is of relevance. More preferably, the dental article is a component of a dental implant system, in particular a dental implant or a dental implant abutment, and/or a tool for installing the dental implant system.

As also mentioned above, a particularly high storage stability can be achieved, if the dental article after the hydrogen peroxide plasma sterilization treatment is packed in a packaging, which is impermeable to gas and therefore also to organic compounds that might be detrimental to the high hydrophilicity achieved.

According to a still further aspect, the present invention therefore also relates to a dental article system comprising
A) a dental article defined above, and
B) a packaging enclosing a packaging interior space in which said dental article is contained, said interior space being sealed from the outside space surrounding the packaging in a gas-tight manner.

In other words, the packaging is made of a material that is impermeable to gas. In order to allow the user to easily check the content, the packaging is preferably at least partially made of a transparent material. Any labels specifying the content are preferably attached to the packaging according to B), since it keeps any potential contamination, such as an adhesive for gluing the label onto the package, away from the interior space and therefore also from the dental article.

As mentioned above, the dental article is placed in a holding container before being packed in the packaging. As also mentioned above, a gas-tight interior can be obtained by covering the gas-permeable parts of the sterilizing container by means of a sealing. In this case, the sterilizing container can be considered a precursor of the packaging.

The fact that hydrogen peroxide plasma treatment leads to the combined effect of achieving an improved hydrophilicity apart from a high sterility of the dental article has been most surprising. The present invention, thus, also relates to the use of a hydrogen peroxide plasma treatment for improving the hydrophilicity of a dental article and/or for improving the storage stability of the hydrophilicity of a dental article.

The present invention is further illustrated by way of the following examples.

EXAMPLES

Experiment 1

Disc-shaped samples of yttria-stabilized zirconia (MZ 111 of CeramTec GmbH) having a diameter of 5 mm and a thickness of 1 mm were treated according to the process described in EP-A-1 982 670 resulting in a surface of a structured topography and of a high hydrophilicity.

The samples were cleaned using oxygen plasma and packed in a sterilization container in the form of a peel bag, whereby Teflon rings were used as spacers for preventing a contact of the samples with the peel bag. The packed samples were then subjected to hydrogen peroxide plasma sterilization.

The samples (packed in the gas-permeable sterilization container) were not subjected to further packaging. After pre-determined periods of storage in the sterilization container, the contact angle of the samples was assessed.

The contact angles were determined using pure water according to the sessile drop method (EasyDrop DSA20E, Krüss GmbH) using a drop size of 0.3 µl. For each time point, three samples were assessed; per sample, one contact angle measurement was made. The contact angles were calculated by the so-called "Circle Fitting" method, i.e. by fitting a circular segment function to the contour of the droplet placed on the surface.

The contact angles determined as a function of the storage time are listed in Table 1.

TABLE 1

Contact angle of samples stored in sterilization container

| Storage time [d] | Sample 1 Contact angle [°] | Sample 2 Contact angle [°] | Sample 3 Contact angle [°] | Mean value Contact angle [°] | Standard deviation Contact angle [°] |
|---|---|---|---|---|---|
| 10 | 2.5 | 4.7 | 3.5 | 3.6 | 1.1 |
| 38 | 4.1 | 5.1 | 4.0 | 4.4 | 0.6 |
| 76 | 3.9 | 4.6 | 5.1 | 4.5 | 0.6 |
| 117 | 5.3 | 4.3 | 6.5 | 5.4 | 1.1 |
| 187 | 6.4 | 5.2 | 5.5 | 5.7 | 0.6 |
| 278 | 9.9 | 0 | 0 | 3.3 | 5.7 |
| 376 | 15.8 | 0 | 0 | 5.3 | 9.1 |
| 556 | 22 | 31.3 | 72.8 | 42.0 | 27.0 |

As shown in Table 1, the samples sterilized with hydrogen peroxide plasma exhibited a "superhydrophilicity" with a contact angle of less than 10° even after a storage time of more than 1 year.

A first sub-set of samples was taken from the peel bag after 10 days of storage and subsequently stored in a well plate where it was exposed to air (sub-set A), whereas for a second sub-set storage in the well plate under air exposure started after 76 days instead of 10 days (sub-set B).

The respective contact angles measured after specified periods of storage in the well plate are given in Table 2 (for sub-set A) and Table 3 (for sub-set B).

TABLE 2

Contact angle of samples according to sub-set A

| Storage time [d] | Sample 1 Contact angle [°] | Sample 2 Contact angle [°] | Sample 3 Contact angle [°] | Mean value Contact angle [°] | Standard deviation Contact angle [°] |
|---|---|---|---|---|---|
| 42 | 59.2 | 47.3 | 13.5 | 40.0 | 23.7 |
| 67 | 111.8 | 76.3 | 76 | 88.0 | 20.6 |
| 149 | 125.9 | 107.3 | 106.8 | 113.3 | 10.9 |

TABLE 3

Contact angle of samples according to sub-set B

| Storage time [d] | Sample 1 Contact angle [°] | Sample 2 Contact angle [°] | Sample 3 Contact angle [°] | Mean value Contact angle [°] | Standard deviation Contact angle [°] |
|---|---|---|---|---|---|
| 12 | 8.7 | 7.9 | 10.5 | 9.0 | 1.3 |
| 39 | 72.4 | 54.2 | 72.5 | 66.4 | 10.5 |
| 69 | 86.6 | 74.9 | 90.1 | 83.9 | 8.0 |
| 111 | 114.8 | 99 | 108.7 | 107.5 | 8.0 |

Thus, after taking the samples from the sterilization container and exposing them to air, a fast increase in the contact angle (and, therefore, a decrease in the hydrophilicity) was determined after relatively short periods of storage.

Experiment 2

In further experiments, the samples described above were packaged in sterilization containers of different volumes.

For a first set (sample 2a), a sterilization container of smaller volume was used than for a second set (sample 2b). In addition, a set of machined samples was assessed (sample 2m), in contrast to the first two sets of samples (sample 2a and 2b), which have been treated according to the technology of EP-A-1 982 670.

After hydrogen peroxide plasma sterilization, the contact angles were determined after several periods of storage, using the same methods as for Experiment 1 above. The results are given in Table 4 below.

TABLE 4

| Storage time [weeks] | Sample 2a Contact angle [°] | Sample 2b Contact angle [°] | Sample 2m Contact angle [°] |
|---|---|---|---|
| 2 | 12.4 | 20.6 | 40.9 |
| 6 | 12.9 | 30.7 | 47.4 |

As shown in Table 4, the samples that have been treated and stored in the smaller sterilization container exhibit lower contact angles at relatively short storage times.

Experiment 3

Zirconia implants made of the material specified in the context of Experiments 1 and 2 above were placed in a sterilization container and were subjected to a hydrogen peroxide plasma sterilization treatment according to the present invention.

For three samples, the chemical composition of the thread portion was analysed by means of XPS after three months of storing.

For comparative reasons, samples, which have not been subjected to a hydrogen peroxide plasma treatment, but which apart from that correspond to the ones mentioned above, have been analysed using XPS (samples $3.1c_1$, $3.2c_1$ and $3.3c_1$). Further comparative examples (samples $3.1c_2$, $3.2c_2$ and $3.3c_2$) were prepared by subjecting samples to an ethylene oxide (EO) treatment instead of a hydrogen peroxide plasma treatment, but which apart from that correspond to the ones mentioned above.

XPS spectra were acquired on a PHI500 VersaProbe spectrometer (ULVAC-PHI INC.) equipped with a focused scanning monochromatic Al—$K_\alpha$ source (1486.6 eV). The photoelectrons were detected at an angle of 45° to the surface normal. The measurements were performed with a spot size of 0.2 mm.

The results are given in Table 5.

TABLE 5

Atomic percentage of elements present on the surface of the samples determined by XPS

|  | Zr | Y | C | O | Si | F |
|---|---|---|---|---|---|---|
| Sample 3.1; $H_2O_2$-plasma treated | 27.6 | 1.1 | 19.1 | 52.1 | 0.0 | 0.0 |
| Sample 3.2; $H_2O_2$-plasma treated | 26.5 | 1.1 | 21.5 | 50.3 | 0.0 | 0.6 |
| Sample 3.3; $H_2O_2$-plasma treated | 27.3 | 1.1 | 20.3 | 51.3 | 0.0 | 0.0 |
| Sample $3.1c_1$; non-treated (comp.) | 22.5 | 0.8 | 34.7 | 41.2 | 0.9 | 0.0 |
| Sample $3.2c_1$; non-treated (comp.) | 27.0 | 1.1 | 23.0 | 48.9 | 0.0 | 0.0 |
| Sample $3.3c_1$; non-treated (comp.) | 27.7 | 1.1 | 20.8 | 50.4 | 0.0 | 0.0 |
| Sample $3.1c_2$; EO-treated (comp.) | 26.3 | 1.1 | 21.3 | 51.3 | 0.0 | 0.0 |
| Sample $3.2c_2$; EO-treated (comp.) | 25.6 | 0.9 | 24.8 | 48.7 | 0.0 | 0.0 |
| Sample $3.3c_2$; EO-treated (comp.) | 25.8 | 1.0 | 27.7 | 45.5 | 0.0 | 0.0 |

Also, the contact angles of both the samples treated according to the present invention and the comparative samples have been determined using DCA measurements.

To this end, the advancing water contact angle was tensiometrically examined by the Wilhelmy method by means of a tensiometer (Lauda TE 3, Lauda Dr. R. Wobser GmbH & Co. KG). The resulting contact angles are given in Table 6.

TABLE 6

Contact angle measurement

|  | Contact angles [°] |
|---|---|
| Sample 3.1; $H_2O_2$-plasma treated | 0.0 |
| Sample 3.2; $H_2O_2$-plasma treated | 0.0 |
| Sample 3.3; $H_2O_2$-plasma treated | 0.0 |
| Sample $3.1c_1$; non-treated (comp.) | 100.1 |
| Sample $3.2c_1$; non-treated (comp.) | 114.7 |
| Sample $3.3c_1$; non-treated (comp.) | 115.3 |
| Sample $3.1c_2$; EO-treated (comp.) | 87.8 |
| Sample $3.2c_2$; EO-treated (comp.) | 77.4 |
| Sample $3.3c_2$; EO-treated (comp.) | 86.1 |

As shown in Table 6, the process of the present invention leads to superhydrophilic samples, whereas the comparative samples remain hydrophobic.

Table 7 shows the proportion of functional groups, in which the carbon atoms are present, for the samples according to the present invention in comparison to the non-treated samples:

TABLE 7

|  | C1s C—C | C1s C—O | C1s COO |
|---|---|---|---|
| Sample 3.1; $H_2O_2$-plasma treated | 67.8 | 14.2 | 18.0 |
| Sample 3.2; $H_2O_2$-plasma treated | 67.4 | 16.3 | 16.4 |
| Sample 3.3; $H_2O_2$-plasma treated | 62.7 | 17.6 | 19.7 |
| Sample $3.1c_1$; non-treated (comp.) | 78.3 | 14.8 | 6.9 |
| Sample $3.2c_1$; non-treated (comp.) | 74.6 | 15.8 | 9.5 |
| Sample $3.3c_1$; non-treated (comp.) | 72.7 | 16.0 | 11.3 |

As shown in Table 5, the content of carbon in the samples according to the present invention and in the samples according to the comparative example are comparable. However, the content of carboxyl groups is much higher for the samples of the present invention compared to the non-treated samples, as shown in Table 7. This higher content of carboxyl groups has been shown to go along with a higher hydrophilicity.

The higher proportion of carboxyl groups in the samples of the present invention is at the cost of the proportion of alkane groups, the proportion of carbonyl groups being comparable for the samples according to the present invention and the non-treated comparative samples.

Experiment 4

In further experiments, the influence of a typical holding container of a dental article, specifically of a blister of a dental implant, on the dental article's hydrophilicity was assessed.

To this end, six samples (4.1 to 4.6) of the same material and topography as specified in Experiment 1 above were, after oxygen plasma cleaning, arranged in a Teflon insert and placed in a blister used for SLA® implants (from Institut Straumann AG) before being packaged in a sterilization container in the form of a Tyvek bag under laminar flow. The samples were then subjected to hydrogen peroxide plasma sterilization.

The development of the contact angle as a function of the storage time is given in Table 8.

TABLE 8

| Storage time (weeks) | Sample 4.1 Contact angle [°] | Sample 4.2 Contact angle [°] | Sample 4.3 Contact angle [°] | Sample 4.4 Contact angle [°] | Sample 4.5 Contact angle [°] | Sample 4.6 Contact angle [°] | Mean value Contact angle [°] | Standard deviation Contact angle [°] |
|---|---|---|---|---|---|---|---|---|
| 3 | 0.0 | 9.6 | 20.9 | 0.0 | 14.0 | 0.0 | 7.4 | 8.9 |
| 6 | 10.4 | 0.0 | 0.0 | 27.8 | 0.0 | 6.2 | 7.4 | 10.9 |
| 11 | 16.8 | 0.0 | 0.0 | 0.0 | 13.5 | 0.0 | 5.1 | 7.9 |
| 18 | 0.0 | 0.0 | 0.0 | 0.0 | 0.0 | 0.0 | 0.0 | 0.0 |

As shown in Table 8, the samples treated according to the present invention were superhydrophilic exhibiting a contact angle of less than 10° even after storage for 18 weeks.

Experiment 5

For comparative reasons, a further set of samples was treated using plasma techniques other than hydrogen peroxide plasma sterilization. Specifically, sample discs of the same material and surface topography as mentioned, but having a diameter of 15 mm and a thickness of 1.2 mm were placed in a sterilization container in the form of a Tyvek bag. A first set of samples was treated using an O2 plasma device generating a "harsh" plasma with a high kinetic input (Tepla) and a second set was treated using an ArH$_2$ plasma device generating a moderate plasma (UCP).

The characteristics of the devices used are given in Table 9 below.

TABLE 9

| Device | Gas | Flux [sccm] | Power [W] | Time [min] |
|---|---|---|---|---|
| Tepla | O$_2$ | 100 | 200 | 25 |
| UCP | ArH$_2$ | 100 | 500 | 25 |

After 3 weeks and 6 weeks of storage, the contact angle was measured using the methods given above. The mean values of the measurements (ten samples for each the first and the second set) as well as the standard deviation are given in Table 10.

TABLE 10

| | O$_2$ Plasma | | ArH$_2$ Plasma | |
|---|---|---|---|---|
| Storage [weeks] | Mean value of contact angle [°] | Standard deviation of contact angle [°] | Mean value of contact angle [°] | Standard deviation of contact angle [°] |
| 3 | 84.0 | 48.2 | 80.0 | 29.5 |
| 6 | 108.9 | 14.3 | 98.9 | 18.1 |

As evidenced in Table 10, all the samples that were treated using O$_2$ plasma or an ArH$_2$ plasma became hydrophobic within a relatively short storage period, exhibiting contact angles of about 100° or higher after 6 weeks. Thus, the effect achievable by the hydrogen peroxide plasma sterilization treatment, namely an improved hydrophilicity and a high storage stability of the hydrophilicity, were not achieved using the alternative plasma sterilization treatments.

Experiment 6

Samples as described in Experiment 1 were after the treatment according to the technology of EP-A-1 982 670 stored in a glass dish with a cover.

After 4.5 months of storage, the contact angles were measured using the sessile drop method described in the context of Experiment 1.

The samples were then packed in a Tyvek bag and subjected to hydrogen peroxide plasma sterilization.

Twelve days after hydrogen peroxide plasma sterilization, the contact angles were again measured.

With regard to the contact angle measurements, 5 samples (6.1 to 6.5) were analysed before sterilization and 10 samples (6.1 to 6.10) were analysed after sterilization (i.e. the 5 samples that were analysed prior to sterilization and 5 further samples). For the measurements before sterilization, a drop size of 0.3 µl was used, while for the measurements after sterilization a drop size of 0.1 µl was used. In both cases, the contact angles were calculated by the "Circle Fitting" method (see Experiment 1).

The results of the contact angle measurement are shown in Table 11.

TABLE 11

| | Contact angle before sterilization [°] | Contact angle after sterilization [°] |
|---|---|---|
| Sample 6.1 | 125.3 | 6.6 |
| Sample 6.2 | 136.2 | 7.9 |
| Sample 6.3 | 124.6 | 5.7 |
| Sample 6.4 | 118.2 | 5.9 |
| Sample 6.5 | 127.1 | 9.5 |
| Sample 6.6 | — | 13.0 |
| Sample 6.7 | — | 6.4 |
| Sample 6.8 | — | 5.1 |
| Sample 6.9 | — | 7.4 |
| Sample 6.10 | — | 13.5 |
| Mean value | 126.3 | 8.1 |
| Standard deviation | 6.5 | 3.0 |

As shown in Table 11, the process of the present invention led to a considerable increase in the hydrophilicity of the samples. Specifically, hydrophobic surfaces were transformed into superhydrophilic surfaces by the process of the invention.

Regarding the sterile dental article system of the present invention, the concept is further illustrated by means of attached FIG. 1 showing a dental article system comprising a dental article and a packaging enclosing an interior space, in which the dental article is arranged.

As shown in FIG. 1, a dental article 10 in the form of a dental implant 100 is placed in a holding container 12 and, in this form, arranged in a sterilization container 14. The sterilization container 14 containing the dental implant 100 arranged in the holding container 12 is again arranged in a packaging 16 enclosing an interior space 18, which is sealed from the outside space surrounding the packaging in a gas-tight manner.

When carrying out the process of the present invention, an initial dental implant 100 is in a first step placed in the holding container 12, allowing the initial dental article to be held safely in place. In a second step, the holding container 12 with the dental implant 100 placed therein is enclosed in the sterilization container 14 and, in this form, is subject to hydrogen peroxide plasma treatment. In order for the hydrogen peroxide gas and plasma get into contact with the dental implant's surface, the sterilization container 14 is at least partially made of a gas-permeable membrane material.

Due to the adventitious contamination layer formed on the initial dental implant, carbon-containing compounds are present, which during the hydrogen peroxide plasma treatment are converted to form a carboxylic group attached to the surface of the dental implant 100, ultimately giving rise to a high long-term hydrophilicity.

Finally, the sterilizing container 14 enclosing the holding container 12 with the treated dental implant 100 is enclosed in the packaging 16 which—owed to the fact that it is sealed in a gas-tight manner—prevents the sterilizing container 14 and ultimately the dental implant 100 from being contaminated, which further contributes to the high hydrophilicity to be maintained over a long term.

Alternatively to packing the sterilizing container 14 in a separate packaging, a gas-tight interior space can also be achieved by covering the permeable parts of the sterilization container 14 using e.g. a gas-impermeable foil or sheet.

The invention claimed is:

1. A process for providing a dental article, in which at least a portion of a surface of the dental article exhibits a contact angle of less than 45°, the process comprising:
    a) providing an initial dental article; and
    b) subjecting the initial dental article to a hydrogen peroxide plasma treatment,
    wherein:
        a carbon-containing compound is present on a surface of the initial dental article,
        the hydrogen peroxide plasma treatment of step b) is carried out in the presence of the carbon-containing compound,
        during the hydrogen peroxide plasma treatment, the carbon-containing compound is converted to form a carboxylic group attached to the surface of the dental article, and
        a hydrophilicity of the dental article after the dental article is subjected to the hydrogen peroxide plasma treatment in step b) is higher than a hydrophilicity of the initial dental article provided in step a).

2. The process according to claim 1, wherein in step b) the initial dental article is sterilized.

3. The process according to claim 1, wherein step a) includes the sub-step of
    a') placing the initial dental article in a holding container which is open in a manner such to allow hydrogen peroxide gas and plasma to get in contact with at least a part of the surface of the initial dental article.

4. The process according to claim 1, further comprising
    c) packing the dental article obtained in step b) in a packaging enclosing an interior space, said interior space being sealed from the outside space surrounding the packaging in a gas-tight manner.

5. The process according to claim 4, wherein the packing according to step c) is performed immediately after the dental article is sterilized by the hydrogen peroxide plasma treatment according to step b).

6. The process according to claim 4, wherein step b) includes prior to the hydrogen peroxide plasma treatment the further sub-step of
    b') arranging the initial dental article in a sterilization container, which is closed and which comprises a membrane material that is permeable to hydrogen peroxide gas and plasma.

7. The process according to claim 6, wherein after the hydrogen peroxide plasma treatment the dental article is stored in the sterilization container.

8. The process according to claim 6, wherein the initial dental article is placed in a holding container and arranged in the sterilization container.

9. The process according to claim 1, wherein the surface of the dental article obtained in step b) has a contact angle of less than 20°.

10. The process according to claim 1, wherein the dental article is made of metal or ceramic.

11. The process according to claim 1, wherein the dental article is made of zirconia.

12. The process according to claim 1, further comprising subjecting the surface of the dental article to a surface roughening treatment before step a).

13. The process according to claim 12, wherein the surface roughening treatment comprises:
    sandblasting the surface, followed by
    acid etching the sandblasted surface using an etching solution containing hydrofluoric acid.

14. The process according to claim 1, wherein the carbon-containing compound is present in the form of an adventitious contamination layer on the surface of the initial dental article.

15. A dental article obtainable by the process according to claim 1, the surface of the dental article being at least partially functionalized with carboxylic groups attached thereto.

16. The dental article according to claim 15, the dental article being a component of a dental implant system.

17. A dental article system comprising
    A) the dental article according to claim 15, and
    B) packaging enclosing a packaging interior space in which the dental article is contained, said interior space being sealed from the outside space surrounding the packaging in a gas-tight manner.

18. The dental article system according to claim 17, wherein the packaging is at least partially made of transparent material.

19. A method of improving the hydrophilicity of a dental article, the method comprising:
    subjecting the dental article to a hydrogen peroxide plasma treatment,
    wherein:
        the dental article contains a carbon-containing compound on a surface thereof, and during the hydrogen peroxide plasma treatment, the carbon-containing compound is converted to form a carboxylic group attached to the surface of the dental article, and
        the hydrophilicity of the dental article is increased after the dental article is subjected to the hydrogen peroxide plasma treatment.

20. The method according to claim 19, wherein at least a portion of the surface of the dental article exhibits a contact angle of less than 45° after the hydrogen peroxide plasma treatment.

* * * * *